United States Patent
Sakai

(10) Patent No.: US 6,270,453 B1
(45) Date of Patent: Aug. 7, 2001

(54) BENDING DEVICE FOR EXAMINING INSERTION TUBE

(75) Inventor: Toshinori Sakai, Yokohama (JP)

(73) Assignee: Suzuki Motor Corporation (JP)

( * ) Notice: Subject to any disclaimer, the term of this patent is extended or adjusted under 35 U.S.C. 154(b) by 0 days.

(21) Appl. No.: 09/472,543

(22) Filed: Dec. 27, 1999

(30) Foreign Application Priority Data

Dec. 28, 1998 (JP) .................................................. 10-373850

(51) Int. Cl.[7] .......................................................... A61B 1/00
(52) U.S. Cl. ................................................................ 600/141
(58) Field of Search ...................................... 600/101, 114, 600/141, 139, 121, 140, 142, 585; 606/49, 46; 604/21, 114, 164

(56) References Cited

U.S. PATENT DOCUMENTS

| | | | |
|---|---|---|---|
| 3,162,214 | * | 12/1964 | Bazinet, Jr. ............................ 604/114 |
| 3,557,780 | * | 1/1971 | Sato ..................................... 600/141 |
| 4,686,963 | * | 8/1987 | Cohen et al. ......................... 600/141 |
| 4,834,069 | * | 5/1989 | Umeda .................................. 600/142 |
| 5,005,558 | * | 4/1991 | Aomori ................................. 600/141 |

FOREIGN PATENT DOCUMENTS 5-253172    10/1993   (JP) .

* cited by examiner

Primary Examiner—Eric F. Winakur
Assistant Examiner—Pamela L Wingood
(74) Attorney, Agent, or Firm—Morrison Law Firm

(57) ABSTRACT

Multiple ring-shape cylindrical members (3) and four wires (4) that link these cylindrical members (3) in a tubular shape are provided. Each cylindrical member (3) comprises two first protruding parts (33) which protrude from the top end face (31) and are formed at both ends of a first diameter (D1), two second protruded parts (34) which protrude from the bottom end face (32) and are formed at both ends of a second diameter (D2), two first small cylindrical members (35) for wire insertion mounted on the outer circumferential face of the cylindrical member respectively at the vicinity of each protruded part (33), and two second small cylindrical members (36) mounted on the outer circumferential face of the cylindrical member respectively at the vicinity of each second protruded part (35), and the first diameter (D1) and the second diameter (D2) are approximately perpendicular.

12 Claims, 9 Drawing Sheets

Fig. 1

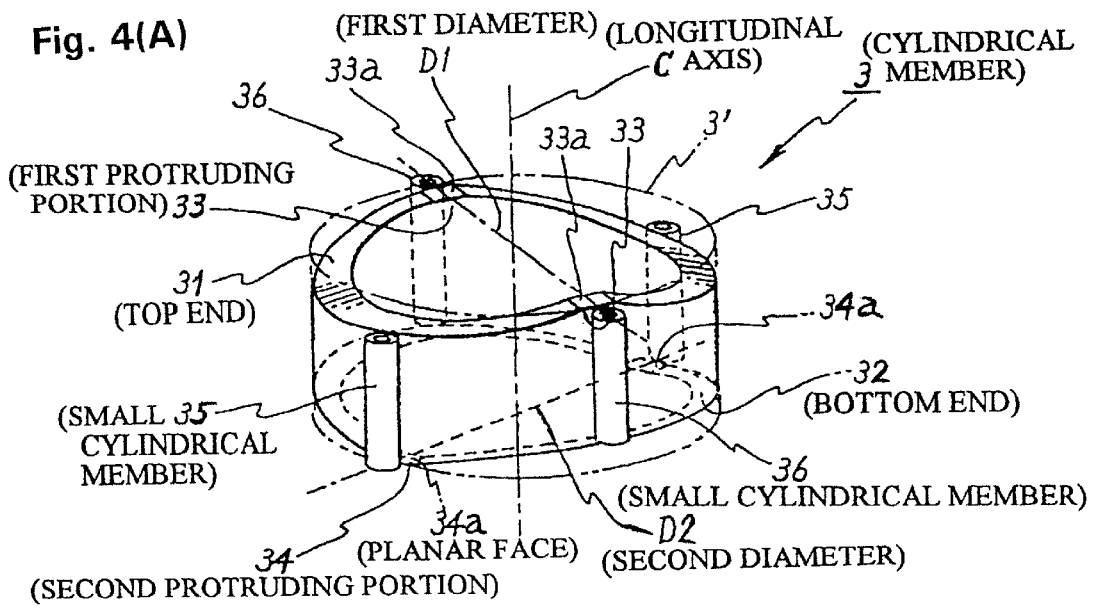
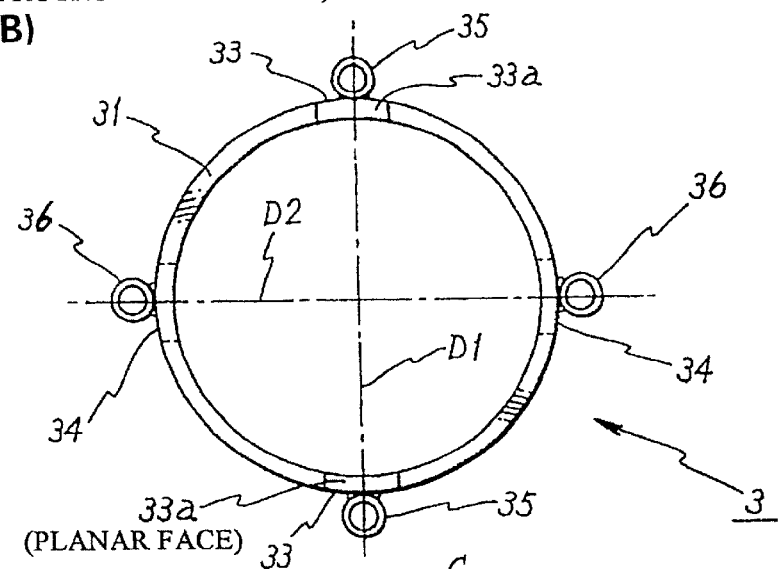
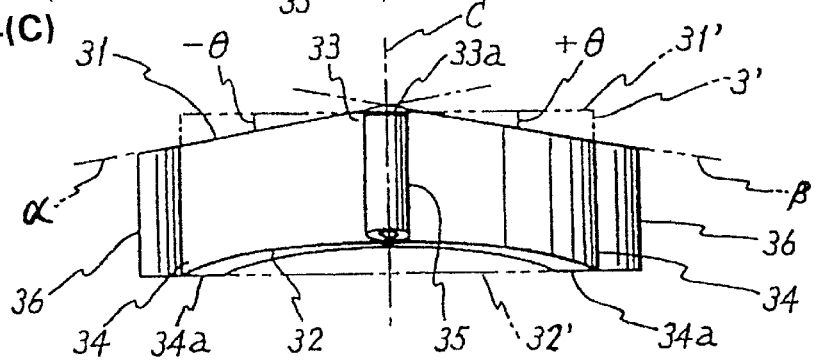

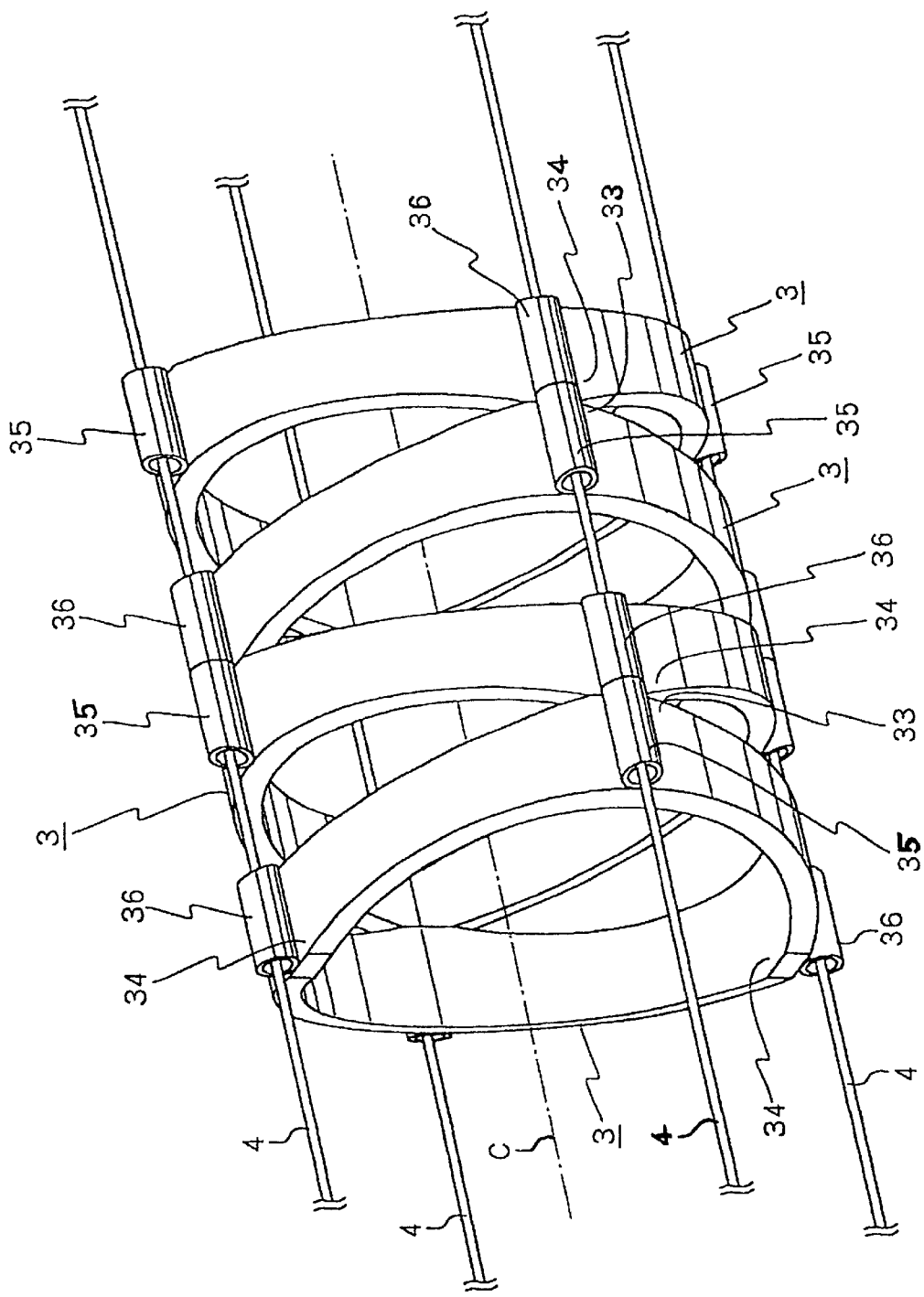

BENDING DEVICE FOR EXAMINING INSERTION TUBE

FIELD OF THE INVENTION

The present invention relates to a bending device for an examining insertion tube. In particular, it relates to a bending device mounted to an examining insertion tube which is for observing a narrow space where a man cannot directly enter such as piping of city water, the inside part of a human body, etc.

BACKGROUND OF THE INVENTION

An examining insertion tube is a promising examination apparatus, which is used for observing the inside of a narrow space (inside of a pipe or a gap, etc.) where human body cannot enter or for observing the state in the vessel or the organs inside the human body without cutting to open the human body. This examining insertion tube generally has an observation means at the head end and an operating mechanism at the bottom end, and is designed for the end portion to be bent in any direction by the operating mechanism.

As a conventional technology, a freely flexible tube (Japanese Patent Application Nos. Hei 5[1993]-253171 and 253172) which provides an observation device around the head end portion and a bending mechanism which bends the observation device in a prescribed direction can be cited.

The bending mechanism is provided with multiple joint members and a bending application means which energizes the bending operation in each joint member and this bending application means is comprised of a wire-like shape memory alloy stretched between the joint members and a heater which heats this shape memory alloy. Namely, according to this constitution, the heated shape memory alloy contracts to its original length and application in the bending operation between the joint members is achieved by utilizing the tensile force [generated] during this contraction.

PURPOSE OF THE INVENTION

However, the aforementioned conventional example has a bending application means between each joint and the bending application means comprises heating a shape memory alloy, thus there is an inconvenience in making the device complex as a whole, causing increase in the number of parts, and as a consequence, generating a decrease in productivity and an increase in the product cost.

Also, control of the bending amount by heating is very difficult, so there is also the difficulty of operating the head end portion freely in the prescribed direction.

Furthermore, the joints are rotatably linked by a fixed pin, so the manufacturing process in this section becomes complex, which causes further decreases in productivity.

The present invention seeks to improve on the inconveniences of the aforementioned conventional example and to provide a bending device of high operability and productivity for an examining insertion tube.

SUMMARY OF THE INVENTION

The present invention provides a bending device of an examining insertion tube which is inserted in an examining object to examine the inside. The bending device bends the head end portion of the examining insertion tube and comprises multiple ring-shape cylindrical members and four wires which link the multiple cylindrical members in a tubular manner (or in a tubular shape).

Each cylindrical member has two first protruded portions which protrude in the axial direction of the cylindrical member from the top end face of the cylindrical member at both ends of a diameter of a first radial direction of the cylindrical member, two second protruded portions which protrude in the axial direction from the bottom end face of the cylindrical member at both ends of a diameter of a second radial direction of the cylindrical member, two first small cylindrical members in which wires are inserted and which are mounted on the outer circumferential surface of the cylindrical member at the vicinities of the first protruded portions respectively, and two second small cylindrical members in which wires are inserted and which are mounted on the outer circumferential surface face of the cylindrical member at the vicinities of the second protruded portions respectively.

The first radial direction and the second radial direction are approximately perpendicular and each cylindrical member is linked to each adjacent cylindrical member by the wires so that the protruded portions of each cylindrical member may contact mutually.

The mutually adjacent cylindrical members are linked by wires inserted in their small cylindrical members with one end face of one cylindrical member in contact with another end face of the other cylindrical member which is adjacent to the former cylindrical member. Because of a wire inserted into each small cylindrical member, the two first protruded portions of the former cylindrical member and the two second protruded portions of the latter cylindrical member mutually contact on the surfaces of such protruded portions.

For example, the first protruded part of the middle cylindrical member contacts the second protruded part of the adjacent upper cylindrical member such that the upper cylindrical member pivots freely on the top surfaces of these protruded portions as the fulcrum (around the diameter linking the two first protruded portions in the first radial direction). Similarly, since the second protruded portions of the middle cylindrical member contacts the first protruded portions of the adjacent lower cylindrical member such that the lower adjacent cylindrical member pivots freely on the top surfaces of the these protruded portions as the fulcrum (around the diameter linking the two second protruded portions in the second radial direction).

Therefore, the upper, middle and lower adjacent cylindrical members enable a bending motion with two degrees of freedom. Since it is possible to make such type of bending motion freely with the three cylindrical members, it is also possible for the head end portion to make a bending motion in any direction.

The bending motion of all linked cylindrical members is made by applying a tensile force to each wire. That is, the space between the sections of adjacent cylindrical members which are not the protruded portions contracts when a tensile force is applied to one wire, which is greater than that applied to any other wire. Thus, the examining insertion tube can be bent at the head end portion towards the wire. Similarly, it is possible to bend the head end portion in a direction towards one wire among the others by applying a tensile force to the one wire. It is Also possible to bend the head end portion in a combined direction by applying tensile forces simultaneously to two adjacent wires.

The invention further provides a bending device of an examining insertion tube further comprising a flat face which is approximately perpendicular to the axial direction of the cylindrical member at the top end surface of each protruded portion. Thus, the flat faces at the top end surfaces of the protruded portions mutually contact closely with those of the adjacent cylindrical member so that it may be easy to keep an upright position by applying the same degree of tensile force to each wire.

The invention yet further provides a bending device of an examining insertion tube which is inserted inside of an examined object and bends the head end portion of an examining insertion tube. The vending device comprises multiple ring-shape cylindrical members and four wires which link the multiple cylindrical members in a tubular manner.

Each cylindrical member comprises two first small cylindrical members which are fixed on the outer circumferential surface of the cylindrical member to be aligned parallel to the axial direction of the cylindrical member and to protrude from one end face of the cylindrical member and through which two wires of the aforementioned wires are passed and two second small cylindrical members which are fixed on the outer circumferential surface of the cylindrical member to be aligned parallel to the axial direction of the cylindrical member and to protrude from one end face of the cylindrical member and through which the two rest wires of the aforementioned wires are passed The two first small cylindrical members are also disposed at both ends of the diameter in the first radial direction the cylindrical member and the two second small cylindrical members are disposed at both ends of the diameter in the second radial direction, which is approximately perpendicular to the first radial direction. Adjacent cylindrical members contact with each other on the end surfaces of the small cylindrical members of the adjacent cylindrical members and are linked by the wires.

In such configuration, the cylindrical members are linked with wires inserted into the corresponding small cylindrical members with the ends of the adjacent cylindrical members facing with each other. By inserting a wire in each small cylindrical member, the two first small cylindrical members of one cylindrical member contact the two small cylindrical members of the other cylindrical member on the end surfaces of the small cylindrical members of the cylindrical members. Then, the cylindrical members pivot on the contact surfaces as the fulcrum and the whole multiple-linked cylinder bends. The bending device operates in a similar manner as mentioned before with respect to the other movements.

The invention further provides a bending device further comprising a flat surface at the end of each small cylindrical member which is approximately perpendicular to the axial direction of the cylindrical member. Thus, such flat planar sections at the extreme ends of the mutually connected small cylindrical members contact closely with each other by applying the same degree of tensile force to each wire so that it may be easy to keep the upright state.

The present invention achieves the aforementioned objective according to each of the aforementioned constitutions.

BRIEF DESCRIPTION OF THE DRAWINGS

FIG. 1 is a perspective view with a partially broken view to illustrate how an embodiment of the present invention is used.

FIG. 4 shows a cylindrical member in the bending device for the examining insertion tube shown in FIG. 1.

FIG. 4(A) is a perspective view of the cylindrical member.

FIG. 4(B) is a top view of the cylindrical member.

FIG. 4(C) is a front view of the cylindrical member.

FIG. 5 is a perspective view of linked cylindrical members, each of which is shown in FIG. 4, to illustrate a linked state.

FIG. 8 shows another type of cylindrical member of another embodiment.

DETAILED DESCRIPTION OF THE PREFERRED EMBODIMENT

Figure 1:
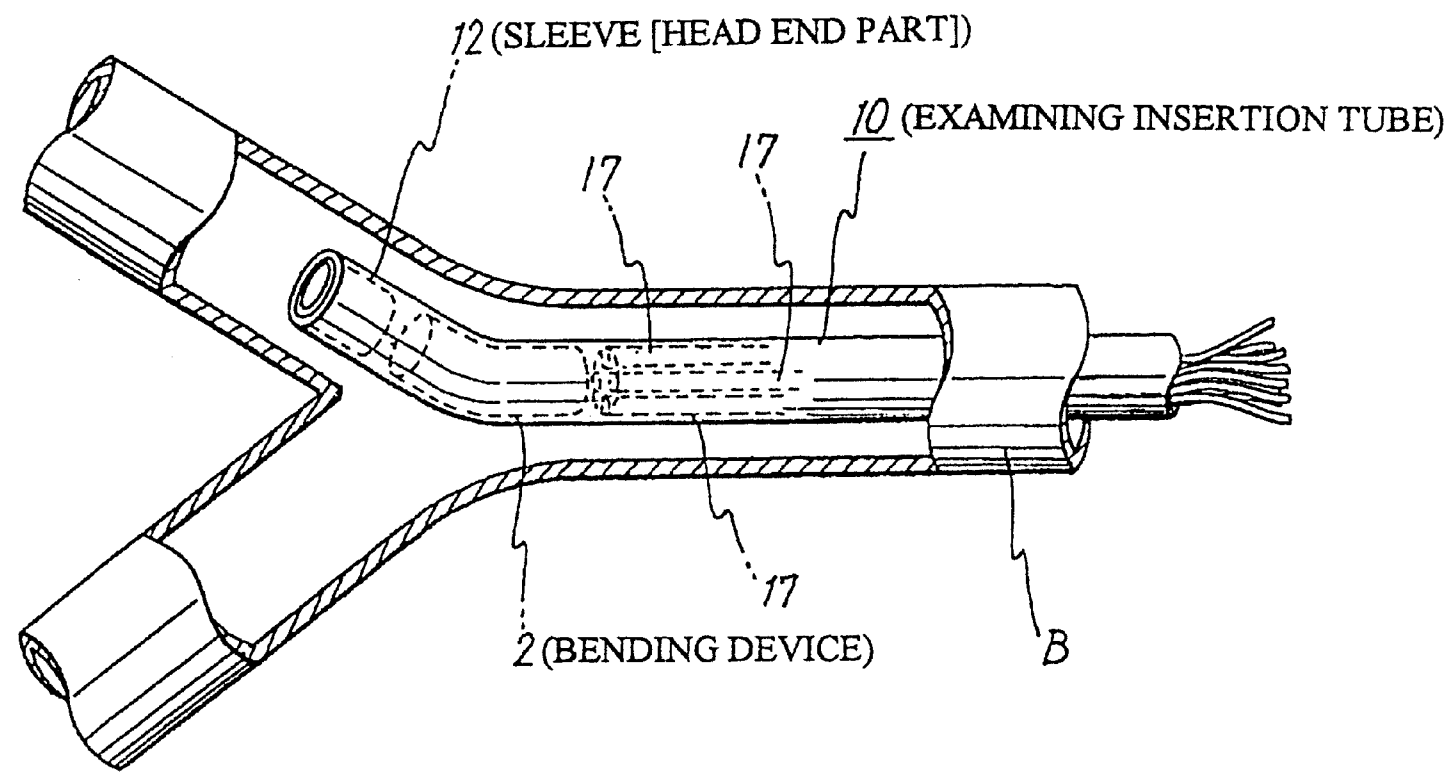
Figure 2:
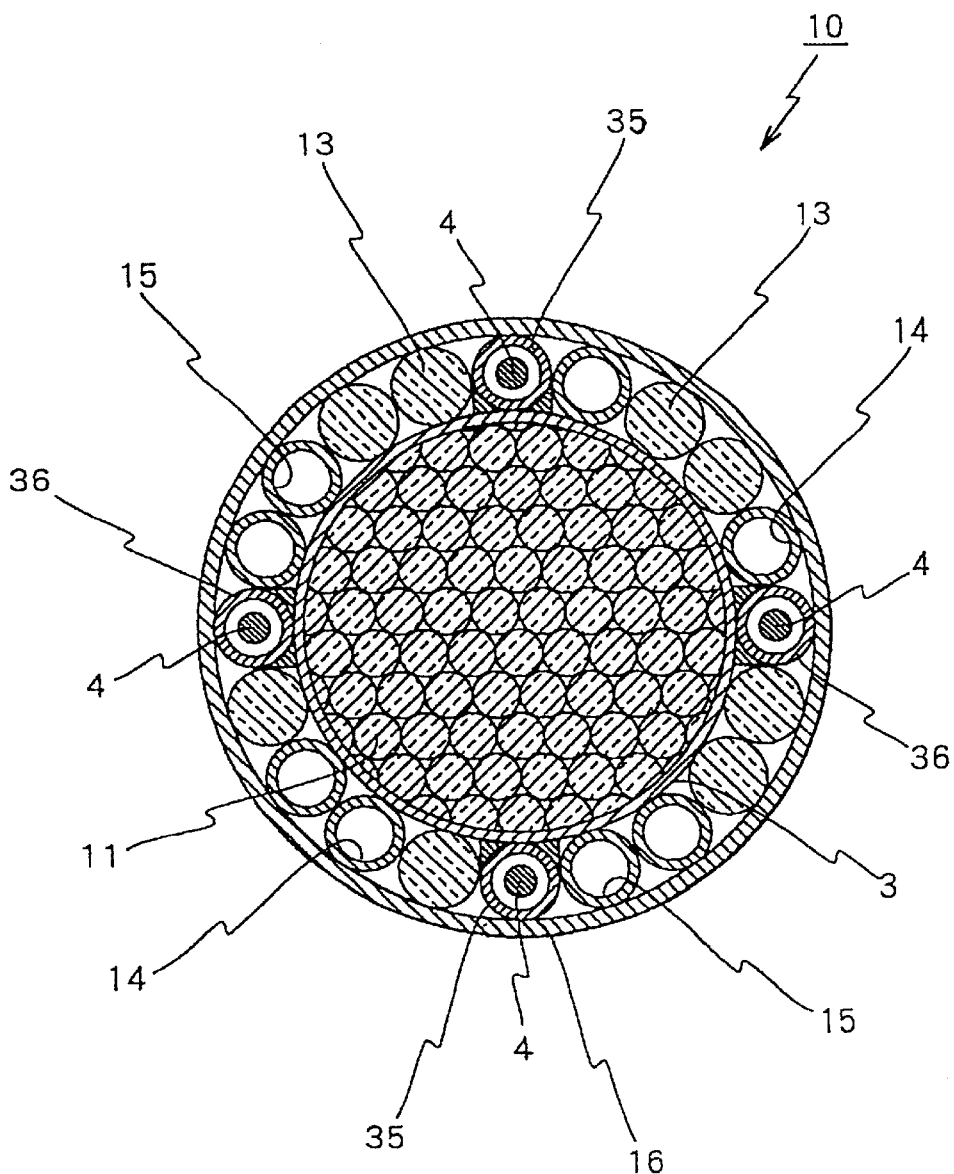
FIG. 2 is a cross-sectional view of an examining insertion tube shown in FIG.

An embodiment of the present invention will be explained based on FIGS. 1 through 7. FIG. 1 shows an examining insertion tube 10 used as a so-called catheter which examines a biological organ inside a human body. This examining insertion tube 10 is inserted from its head (or top or front) end into the examination target and its bottom end is connected to an examination information processor (not shown in the figure). FIG. 1 illustrates a inserted state of this examining insertion tube 10 for examination inside vessel B of the human body.

This examining insertion tube 10 is designed to have an overall length of about 1 [m] and a major diameter of about 1 [mm]. It has a sleeve 12 at the head end to hold an examining means and a bending device 2 which bends the head end portion in a desired direction so as to turn the sleeve 12 in a certain direction. The bending device 2 has multiple ring-shape cylindrical members 3, four wires 4 which link the cylindrical members 3 in a tubular manner, and an operating mechanism 5 which causes a bending motion around the head end portion ahead of the multiple cylindrical members 3 linked by these wires 4. The cylindrical members 3 are designed to be disposed in a certain length range (e.g., 2–10 [cm] from the extreme head end) from the extreme head end of the examining insertion tube 10.

Figure 3:
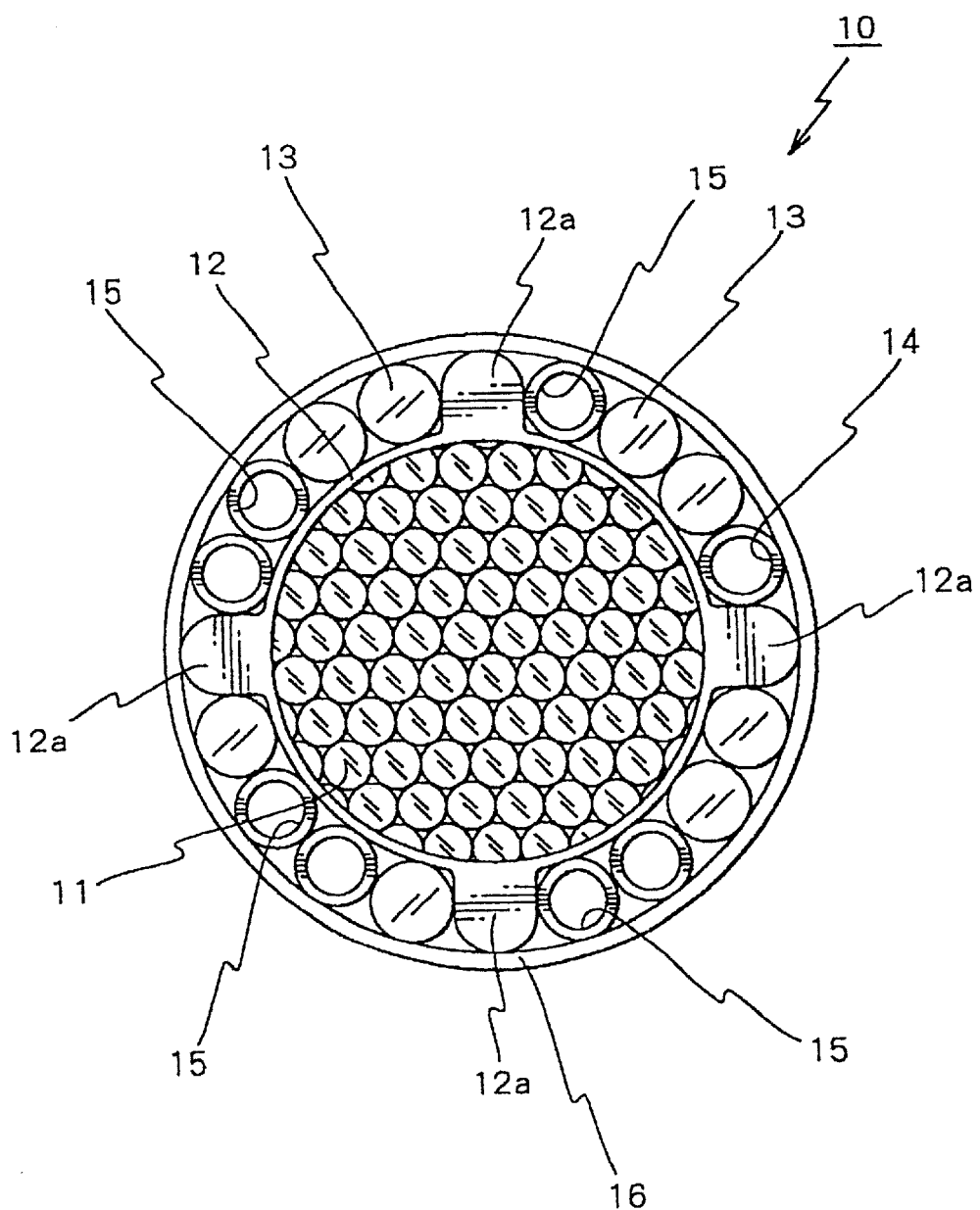
FIG. 3 is a left-side view of the examining insertion tube shown in FIG. 1 to illustrate the extreme top end.

FIG. 2 shows a cross-section cut at a plane which is perpendicular to the longitudinal direction of the examining insertion tube 10. FIG. 3 shows the extreme head end of the examining insertion tube 10 in the longitudinal direction. As shown in FIG. 3, the sleeve 12 is a round cylinder with approximately the same diameter as the cylindrical member 3, and four convex portions 12a corresponding to small cylindrical members 35, 36 to be discussed later are formed on the outer circumferential surface of the sleeve. The extreme head ends of wires 4 are fixed on the backsides of these convex portions 12a.

The sleeve 12 holds the extreme end part of image fibers 11 as an examining means. The image fibers 11 are disposed inside of the sleeve 12 and the cylindrical members 3. The image fiber 11 is composed of bundled multiple optical fibers. A state image of the object into which the head of examining insertion tube 10 is inserted is obtained from the extreme head end of the tube and is transmitted to the aforementioned examination information processor.

Around the sleeve 12 and each cylindrical member 3, light guides 13 comprised of an optical fiber which transmits light to illuminate an object in front of the extreme head end of the examining insertion tube 10, a fluid ejecting tube 14 which supplies fluids such as physiologic saline, a prescribed chemical, etc. to the extreme head end side, and multiple fluid intake tubes 15 which suck fluid from the extreme head end side are disposed. The light guides 13, the fluid ejecting tube 14, and the fluid intake tubes 15 are connected to the aforementioned examination information processor at their rear end parts, respectively.

On the other hand, the examination information processor has a light source for the light guides 13, a means for supplying fluid to the fluid ejecting tube 14, a pump which energizes the suction motion through the fluid intake tubes 15. As a function of the fluid ejecting tube 14, physiologic saline is injected if the field of view of the image fiber 11 is blocked by blood flow when the examining insertion tube 10 is inserted inside vessel B to ensure a field of view in front of the extreme head end, wash, disinfect and supply chemicals to an affected part. A function of the fluid intake tube 15 is to collect excessively injected physiologic saline and a blood sample.

A laser light source may replace the light source of the light guide 13 for illumination in the examination information processor. In this case, a laser beam can be irradiated from the extreme head end of the light guide 13, by way of example, to treat and cure the human body.

The entire face (excluding the head and bottom end faces) of the examining insertion tube 10 is covered with a flexible tube 16. The image fiber 11, the light guide 13, fluid ejecting tube 14, and fluid intake tubes 15 are flexible and extend from the extreme head end part to the tail end part of the examining insertion tube 10 as mentioned above.

Therefore, the image fibers 11, the light guides 13, the fluid ejecting tube 14, and the fluid intake tubes 15 may be freely deformed at the lower portion than the cylindrical member 3 when an external force is applied. Consequently, the examining insertion tube 10 is deformed easily upon receipt of the external force in the portion other than the sleeve 12 and the cylindrical member 3 and is not prevented from insertion when it is inserted into the object to be examined.

An objective lens (omitted being shown in FIG. 3) is mounted on the extreme head end part of the image fiber 11 held by the sleeve 12. This objective lens is held by the sleeve 12 to maintain a distance such that an image is formed on the extreme head end face of the image fiber 11 by the external light coming from the extreme head end of the examining insertion tube 10.

Next, the bending device 2 will be explained. FIG. 4 shows the cylindrical member 3. The cylindrical member 3 is formed into approximately a ring-shape or is formed into a round cylindrical shape in which the length in the direction of the longitudinal axis (or center axis) C is short (length in the direction of the longitudinal axis C is set to be at least shorter than the outer diameter (or major diameter) of the cylindrical member 3, more preferably, a length of ⅓ to ½ of the outer diameter or even shorter). The cylindrical member 3 is made of metal and the outer diameter is set about 0.7 [mm]. This major diameter of the examining insertion tube 10 can be changed according to the application. Each cylindrical member 3 need not be made of a particular metal with respect to its raw material since it is covered by a covering tube 16 and is not in contact with the human body. Other materials (e.g. high polymer material) can be selected in a view of strength, manufacturing cost, etc.

To explain in further detail, the cylindrical member 3 comprises two first protruding parts (or portions) 33, 33, which protrude in the longitudinal axial direction C from a top end face (or one end face) 31 of the cylindrical member 3 and are fixed at both ends of a diameter in a first radial direction D1 ("First Diameter" hereafter) of the cylindrical member 3 and two second protruded parts (or portions) 34, 34, which protrude in the longitudinal axial direction C from a bottom end face (or other end face) 32 of the cylindrical member 3 and are fixed at both ends of a diameter in a second radial direction D2 ("Second Diameter" hereafter) of the cylindrical member 3.

The First Diameter D1 at both ends of which the first protruding parts 33 are positioned is perpendicular to the Second Diameter D2 at both ends of which the second protruding parts 34 are positioned if viewed from the direction of the longitudinal axial direction C (see FIG. 4(B)).

Furthermore, the cylindrical member 3 comprises two first protruding parts 33, 33 across the First Diameter D1. The two first protruding parts 33, 33 are shaped by machining a cylindrical member 3' along two planes α, β which are tilted from one end face 31', which is perpendicular to the longitudinal axial direction C, of the cylindrical member 3' by the angle of ±θ, respectively, as shown in FIG. 4(C). Thus, according to such machining to remove the material from the cylindrical member 3' along the two planes α, β, the machined top end (or one end) face 31 increases the height towards the center line C if viewed from the front (FIG. 4(C)) to form a protruding part 33. In a similar manner another protruding part 33 is made across the First Diameter D1. The two protruding parts are designated the first protruding parts 33, 33.

In the embodiment, the two planes α, β cross in the straight line just above the First Diameter D1 and aligned parallel to the First Diameter D1. The absolute value θ of the tilt angel may be set according to the design specification and range preferably from 5 to 30 degree and more preferably about 15 degree.

In a similar manner, two second protruded parts 34, 34 across the Second Diameter D2 are formed by machining the material symmetrically along two planes (omitted from the figures) which are tilted from an other end (or bottom end) face 32', which are perpendicular to the longitudinal axial direction C.

Also, the extreme top ends of the protruded parts 33, 33, 34, 34 are formed in flat faces (or planar faces) 33a, 33a, 34a, and 34a, respectively, which are approximately perpendicular to the longitudinal axial direction C of the cylindrical member 3. In linked cylindrical members 3, two flat faces 33a, 33a of a cylindrical member contact two flat faces 34a, 34a of the lower adjacent cylindrical member 3.

Furthermore, first and second small cylindrical members 35, 35, 36, 36 which are much smaller than cylindrical member 3 and in which wires 4 are inserted are mounted on the cylindrical member 3. These first small cylindrical members 35, 35 are respectively mounted by soldering, adhesion, or laser welding on the outer circumferential face of the cylindrical member 3 and are oriented in the longitudinal axial direction Cl in the vicinities of the first protruded parts 33, 33. Similarly, the second small cylindrical members 36, 36 are respectively mounted on the outer circumferential face of the cylindrical member 3 and are oriented in the longitudinal axial direction Cl of the cylindrical member 3 at the vicinities of the second protruded parts 34, 34. The minor (or inner) diameter of the cylindrical members 35, 36 is set to be a size capable of freely receiving the wire 4.

In this cylindrical member 3, miniaturization of the diameter of the examining insertion tube 10 is achieved by utilizing the space between a mutually adjacent first small cylindrical member 35 and a second small cylindrical member 36 as the area for arranging the aforementioned light guide 13, the fluid ejecting tube 14, and the fluid intake tubes 15.

Though it will be discussed later, each wire 4 needs to be pulled towards the tail end side of the examining insertion tube 10 relatively to the multiple linked cylindrical members 3 to perform a bending motion of the bending device 2. If cylindrical members 3 in the covering tube 16 are pulled towards the tail end side along with the wires 4, the bending motion cannot be performed well. In order to prevent this, four small tubes 17 (see FIG. 1), which have approximately the same diameter as that of small cylindrical members 35, 36, which are freely deformable, and which have an insertion hole for inserting the wire 4, are disposed from the lowest cylindrical member 3 to the tail end part of the examining insertion tube 10 corresponding to the radial positions of the small cylindrical members 35, 35, 36, 36.

The multiple cylindrical members 3 with the aforementioned structure are lined in the concentric manner of the longitudinal axial direction (FIG. 5). In this examining insertion tube 10, twelve cylindrical members 3 are used but the number can be varied according to the necessary bending angle at the extreme head end part of the examining insertion tube 10. When the bending angle is large, more cylindrical members 3 may be used.

The wires 4 are respectively inserted in small cylindrical members 35, 35, 36, 36 of each cylindrical member 3. At this time, flat faces 33a, 33a at the extreme top ends of the first protruding parts 33, 33 in all cylindrical members 3, which are linked only with the wires 4, contact flat faces 34a, 34a at the extreme bottom ends of the second protruding parts 34, 34 of a lower adjacent cylindrical member 3.

Also, the tail end part of each wire 4 extends to an operating mechanism 5 provided at the tail end part of the examining insertion tube 10 through the aforementioned flexible tube 17. Then, two out of four respective wires 4, 4 inserted into the two small cylindrical members 35, 35 of any cylindrical member 3 are mutually linked at the tail end parts and the other two wires 4, 4 inserted in the two through-holes 36, 36 of the same cylindrical member 3 are mutually linked at the tail end parts. Two linked wires 4, 4 can also be made of single wire which is returned at the tail end side.

At the tail end side of the examining insertion tube 10, the image fibers 11 and the light guides 13, etc. around the periphery of the image fibers 11 are branched off from the four wires 4. Namely, the image fibers 11, etc. are curved outside and separated from the wires 4 and are connected to the examination information processor.

Figure 6:
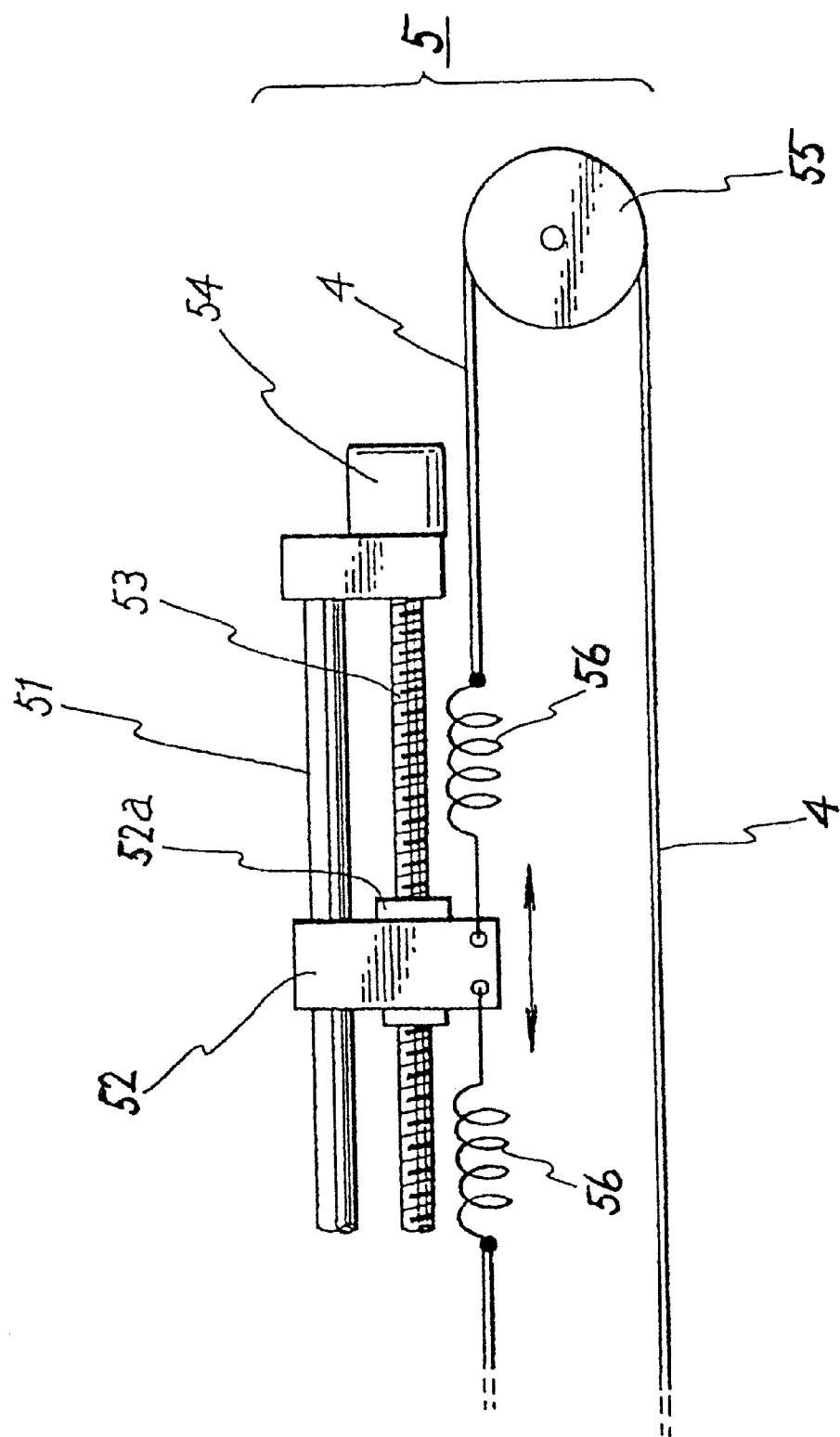
FIG. 6 is a side view of the operating mechanism.

On the other hand, each wire 4 is connected to the operating mechanism 5. The operating mechanism 5 is provided for each linked wire 4. As shown in FIG. 6, the wire 4 which is linked is half wound on a pulley 55 that is one part of the opening mechanism 5 mounted rotatably in the returning section with respect to the wire linkage.

The operating mechanism 5 comprises a guide rail 51 fixed parallel to the wire 4, a slider 52 which is slidable along this guide rail 51, a ball screw 53 disposed parallel to the guide rail 51, a drive motor 54 which rotates and drives this ball screw 53, and the aforementioned pulley 55.

The slider 52 is linked to the linked wire 4 via a tension spring 56. Also, this slider 52 is engaged to the ball screw 53 via a screw receiver 52a and performs a reciprocating movement via the ball screw 53 according to the rotation in the positive and negative directions (or clockwise and counter clockwise rotation) of the drive motor 54. According to the rotation, the tensile force is generated in either one wire 4 or the other wire 4 because they are linked. The tension spring 56 is disposed between the slider 52 and the wire 4 in order to prevent an excess tension to each cylindrical member 3 applied for a bending motion from the operating mechanism 5 via the wire 4. Also, the tensile force can be calculated by providing a sensor which detects the displacement in the length of this tension spring 56 and the bending degree in the linked members composed of cylindrical members 3 can be controlled.

In FIG. 6, only two wires 4 are shown but the operating mechanism 5 for the remaining two wires 4 is provided nearer to the tail end.

Next, the operation of the examining insertion tube 10 will be explained. This examining insertion tube 10 is inserted into the vessel of a human body as shown in FIG. 1 and the state of the inside is observed through the image fibers 11. At this time, if it is needed to bend the extreme head end part (e.g., if it is needed to observe an affected part by turning the extreme head end towards the affected part or if it is needed to proceed in either branch while the inserted part (e.g., tube) is branched, etc.), the operation is performed according to each operating mechanism 5.

Figure 7:
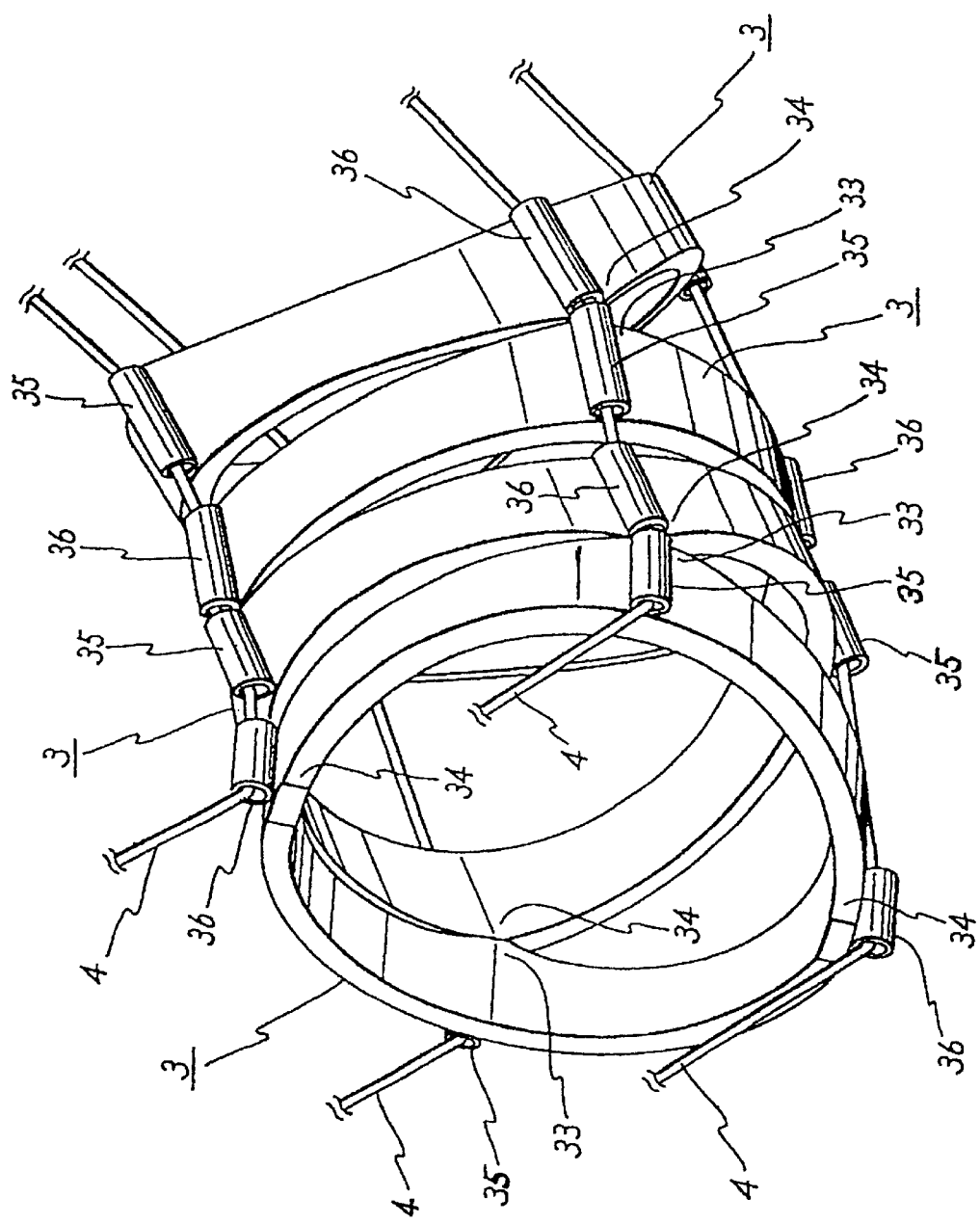
FIG. 7 is a perspective view of linked cylindrical members, which illustrates a bent state of the linked cylindrical members shown in FIG. 5.

The bending motion of the bending mechanism 2 will be explained in greater detail referring to FIG. 7. In the case of one certain cylindrical member 3, flat faces 33a of the two first protruding parts 33 in the cylindrical member 3 contact flat faces 34a of the two second protruding parts 34 of the cylindrical member 3 which is adjacent on the top side such that one of the adjacent cylindrical member 3 may pivot freely on the contacted portions of these protruding parts 33, 34 as the fulcrum (around the First Diameter D1 linking the two first protruding parts 33). Similarly, the flat faces 34a of the two second protruding parts 34 of the cylindrical member 3 contact flat faces 33a of the first protruding parts 33 of the cylindrical member 3 that is adjacent on the bottom side such that the adjacent cylindrical member 3 pivot freely on the contacted portions of these protruding parts 33, 34 as the fulcrum (around the Second Diameter D2 linking second protruding parts 34).

Consequently, when a tensile force is applied to each wire 4 from each operating mechanism 5, the cylindrical member 3 on the most extreme head end side is pulled in the direction of the tensile force and the mutual space between the cylindrical members 3 in the radial area where the wires 4 are pulled by this tensile force is narrowed with respect to all cylindrical members 3. Therefore, the extreme head end part of the examining insertion tube 10 is bent in the direction to which the wire 4 is pulled by the tensile force. In FIG. 7, the bending state of each cylindrical member 3 is shown when a tensile force is applied to the front and top wires 4 in the figure. Thus, applying a tensile force simultaneously with respect to two adjacent wires 4, the extreme head end part of the examining insertion tube 10 can be bent in any direction with two degrees of freedom (including a combined direction).

Since the tensile force applied to the wire 4 performs a bending motion, it is possible to control a bending amount with ease. Furthermore, since a plurality of cylindrical members 3 are linked, the possible bending range can be set freely by varying the number of linked cylindrical members 3.

Each joint is conventionally linked to pivot freely and has a means for performing the bending motion. However, in this embodiment, it is not necessary to use a linking mechanism such as a pin fastener, etc. and it has a structure of linking cylindrical members 3 only with the wire 4. To utilize the wire 4 which operates a bending motion of the cylindrical members 3 it is possible to assemble the cylindrical members 3 by inserting the wire 4 into the wires holding parts of the cylindrical members 3. Consequently, the manufacture and number of parts in the linking structure can be reduced, great improvement in productivity can be achieved, and reduction in the production cost results when compared to the conventional technology. Due to such high productivity and reduced production cost, it is possible to make favorable accommodation for a disposable examining insertion tube for sanitation reasons such as while conducting an examination through insertion into the inside part of a human body, etc.

Furthermore, as mentioned above, the protruding parts 33, 34 are formed by removing the two end parts of the cylindrical member 3 along the tilted two planes so that it is easy to make the protruding parts 33, 34 and to achieve further improvement in productivity. Also, at this time, it is possible to freely set the mobile bending range by changing the setting of the tilt angle in the aforementioned two planes.

Furthermore, in the aforementioned bending mechanism 2, the small cylindrical members 35, 36 are mounted on the outer circumferential face of each cylindrical member 3, through which the wires 4 are inserted. The small cylindrical members 35, 36 can be fixed later by soldering, adhesion, welding, etc., and are fixed on the outer circumferential face of cylindrical member 3 such that it may be easy to manufacture them and therefore, the productivity may be improved. Since it is easy to manufacture them, a smaller cylindrical member 3 than the conventional one can be made and it is beneficial to miniaturize the examining insertion tube 10.

Also, in the case of a structure that inserts the wires 4 into the small cylindrical members 35, 36, the wall thickness of the cylindrical member 3 can be set to be thinner than in the case of providing a through-hole for the wire insertion to the cylindrical member 3 itself, so as to achieve miniaturization in the major diameter of the examining insertion tube 10. Both inside area and outside area of the cylindrical member 3, for example, can be used as the area for arranging the component parts (the light guides 13, the fluid ejecting tube 14, the fluid intake tubes 15, etc.) (see FIG. 2) of the examining insertion tube 10. At the same time, it may be possible to make the weight of each cylindrical member 3 lighter.

Furthermore, the aforementioned small cylindrical members 35, 36 are mounted on the outer circumferential face of the cylindrical member 3 so that the component parts (the light guides 13, the fluid ejecting tube 14, and the fluid intake tubes 15) are to be arranged on the outside of the cylindrical member 3 to achieve miniaturization of the major diameter of the examining insertion tube 10 if compared to the case of mounting the small cylindrical members 35, 36 on the inner circumferential face. The arrangement on the outside of the cylindrical member 3 has more flexibility such as providing softness for the feeling from the outside of the examining insertion tube 10 than the case of arranging all the constituent parts on the inside of cylindrical member 3 (since the wall face of the cylindrical member 3 normally has a fixed hardness in the case that the positioning the light guides 13, the fluid ejecting tube 14, the fluid intake tubes 15, etc. are disposed between the covering tube 16 and the cylindrical member 3 compared to the case that the wall face of the cylindrical member 3 is just inside the covering tube 16).

Therefore, in this embodiment, the feel on the insertion of the extreme head end side of the examining insertion tube 10 has a softness such that it is favorable when, for example, the examination object is a human body or an organism, and the inserting operation itself can be easily executed.

Furthermore, the small cylindrical members 35, 36 are mounted on the outer circumferential face of the cylindrical member 3 so that a greater distance can be maintained from the first diameter or the second diameter of cylindrical member 3 to the wire 4 compared to the case of mounting the small cylindrical members 35, 36 on the inner circumferential face. Consequently, the bending moment for the cylindrical member 3 becomes large when a tensile force is applied to the wire 4. In other words, applying a bending motion with less tensile force becomes possible. Therefore, it may be possible to perform a bending motion smoothly so as to improve the operation of the bending motion.

Furthermore, in bending mechanism 2, the flat faces 33a, 34a that are perpendicular to the longitudinal axial direction C are provided at the extreme head end of protruding parts 33, 34 of the cylindrical member 3 so that it is the advantage for the multiple-linked cylindrical members 3 to easily maintain their upright state since the flat face 33a and the flat face 34a mutually make a contact with the entire face by applying the equivalent tensile force to each wire 4.

Figure 8A:
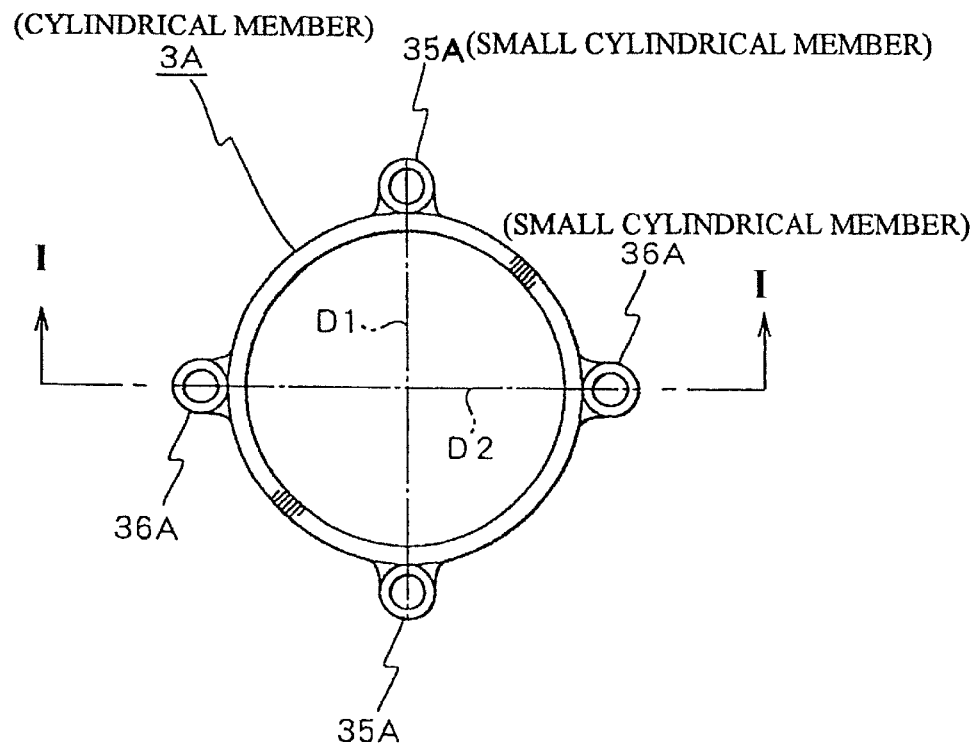
FIG. 8(A) is a top view of the type of cylindrical member.
Figure 8B:
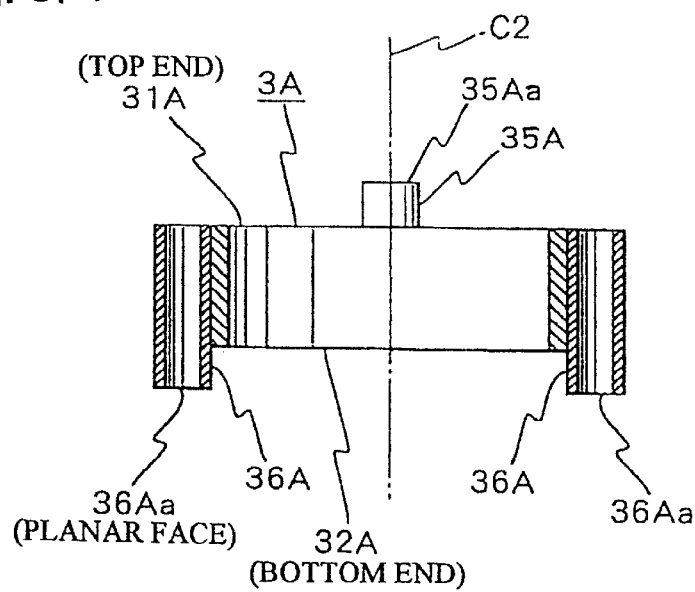
FIG. 8(B) is a cross-sectional view along a Y—Y line in FIG. 8(A).
Figure 9:
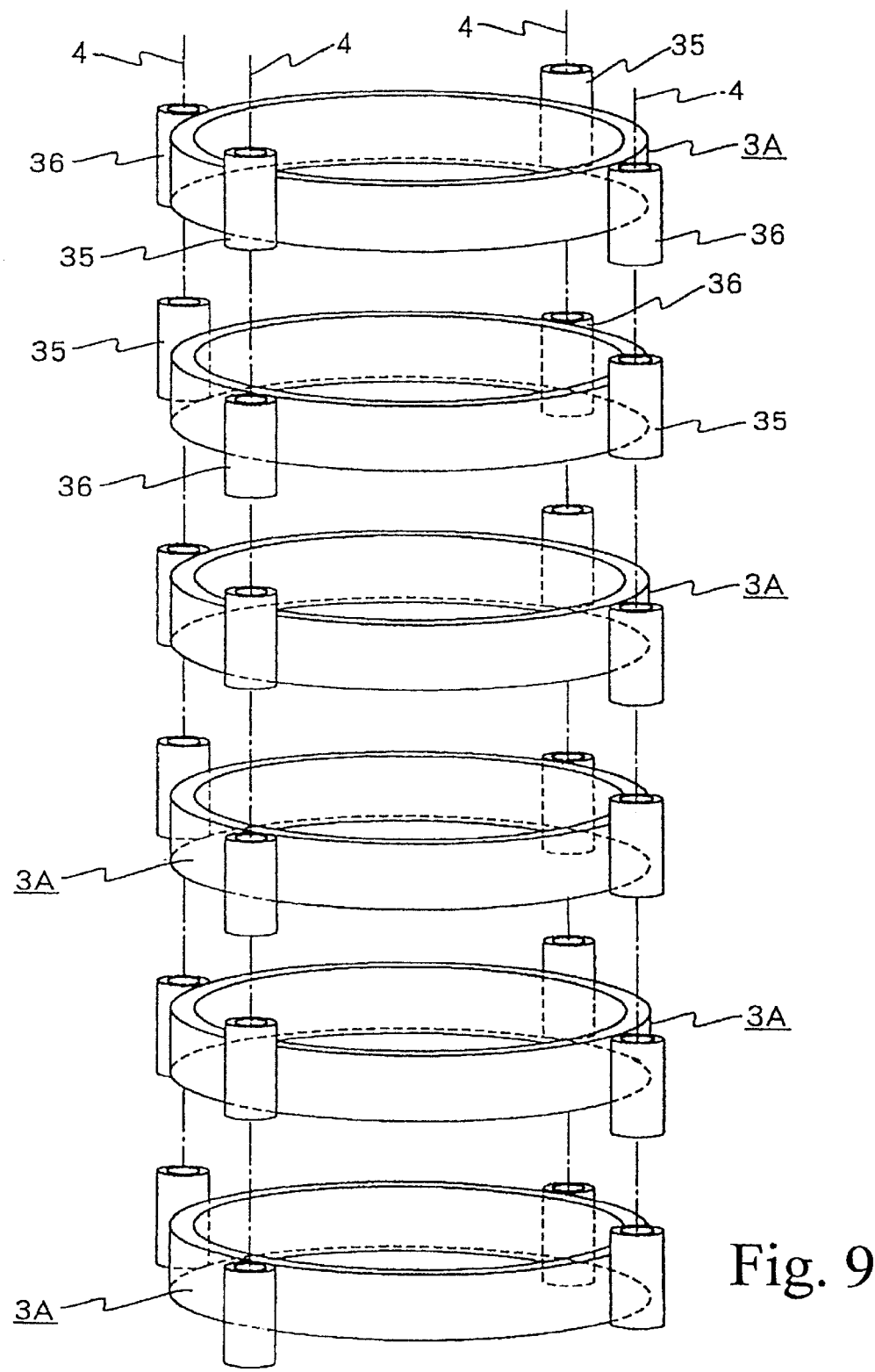
FIG. 9 is a perspective view of linked cylindrical members, each of which is shown in FIG. 8, to illustrate a linked state.

Another embodiment of a cylindrical member 3A that operates in the same manner as the cylindrical member 3 will be explained based on FIGS. 8 and 9. FIG. 8(A) shows a top view of the cylindrical member 3A and FIG. 8(B) shows a cross-section view along the line Y—Y in FIG. 8(A). Also, FIG. 9 shows a perspective view illustrating the arrangement of the cylindrical member 3A. Regarding the cylindrical member 3A, the same parts as the aforementioned cylindrical member 3 are designated with the same references, and a duplicate explanation is omitted.

The cylindrical member 3A differs from the cylindrical member 3 in that two end faces 31A, 32A are formed from a plane perpendicular to the longitudinal axial direction C2. Namely, the cylindrical member 3A itself is not formed with protruding parts. First and second small cylindrical members 35A, 35A, 36A, 36A are mounted on the outer circumferential face of the cylindrical member 3A as is in the cylindrical member 3. These small cylindrical members 35A, 35A, 36A, 36A are mounted in the same arrangement as the cylindrical member 3. Namely, on the outer circumferential face of the cylindrical member 3A, the first small cylindrical members 35A, 35A are mounted on the two ends of any diameter D1 of the cylindrical member 3A, and the two other second small cylindrical members 36A, 36A are mounted on the two ends of the diameter D2 which is perpendicular to the diameter D1. Also, the small cylindrical members 35A, 36A are aligned parallel to the longitudinal axial direction C2, and the minor diameter is set at a size through which the wire 4 can be inserted.

Also, in the cylindrical member 3A, each first small cylindrical member 35A is somewhat protruding from one end (or top end) face 31A, and flat face 35Aa, which is parallel to a plane perpendicular to the longitudinal axial direction C2, is provided at this protruded extreme head end side. Similarly, each second small cylindrical member 36A is somewhat protruding from the other end (or the bottom end) face 32A, and flat face 36Aa, which is parallel to a plane perpendicular to the longitudinal axial direction C2, is provided at this protruding extreme head end side.

Then wires 4 are inserted in the small cylindrical members 35A, 35A, 36A, 36A of the multiple cylindrical members 3A and are linked. At this time, all cylindrical members 3A are linked to their adjacent cylindrical member 3A so that flat face 35A$a$ of the first small cylindrical member 35A of one cylindrical member 3A and flat face 36A$a$ of the second small cylindrical member 36A of the other cylindrical member 3A make contact.

Namely, in cylindrical member 3A, by having mounted two first small cylindrical members 35A protruding from one end face 31A, it operates in the same manner as the aforementioned first protruded part 33. Also, by mounting two second small cylindrical members 36A protruding from the other end face 32A, it functions in the same manner as the aforementioned second protruded part 34.

Consequently, the flat faces 35A$a$ of the two first small cylindrical members 35A of one given cylindrical member 3A contact flat faces 36A$a$ of the two second small cylindrical members 36A of cylindrical member 3A that is adjacent on one side, so one adjacent cylindrical member 3A rotates freely with the contacted section of these flat faces 35A$a$, 36A$a$ as the fulcrum (with diameter D1 composed by linking the two first small cylindrical members 35A as the axis). Similarly, flat faces 36A$a$ of the two second small cylindrical members 36A of pertinent cylindrical member 3A contact flat faces 35A$a$ of the first small cylindrical members 35A of cylindrical member 3A that is adjacent on the other side so the other adjacent cylindrical member 3A rotates freely with the contacted section of these flat faces 35A$a$, 36A$a$ as the fulcrum (with diameter D2 composed by linking the second small cylindrical members 36A as the axis).

According to the structure noted above, the cylindrical member 3A functions in approximately the same manner as the aforementioned cylindrical member 3 and the same effects apply.

Furthermore, in cylindrical member 3A all parts can be easily formed, the two end faces are composed of smooth cylindrical shape members, a process of removal or cutting off becomes unnecessary, and higher productivity can be realized.

As noted above, aforementioned cylindrical members 3, 3A have a structure of holding the wires with small cylindrical members 35, 36, 35A, 36A so that both cylindrical members 3 and 3A can be made into a squeezed-out shape along the longitudinal axis. Consequently, cylindrical members 3 and 3A can be manufactured just by the operation of cutting, hole perforation, etc., along the longitudinal axial direction C, work from the lateral direction in separate processes is unnecessary, and improving the productivity of examining insertion tube 10 becomes possible.

Also, regarding aforementioned cylindrical members 3 and 3A, both cylindrical members 3 and 3A can be squeezed out along the longitudinal axial direction C, C2 so that manufacturing of micro cylindrical members in large volume, and thus achieving high productivity is possible by applying the photoetching technology or dry etching technology used in the semiconductor manufacturing process.
Achievement The invention provides first protruded parts to both end parts of an optional diameter on one end face of a cylindrical member, provides second protruded parts to both end parts of the other diameter which approximately crosses the pertinent diameter on the other end face, and the first protruded part and the second protruded part of multiple cylindrical members continuously arranged are linked in a mutually contacted state such that the cylindrical members can be mutually rotated with a diameter which links the extreme ends of the protruded parts as the axis. Therefore, the extreme end part of the examining insertion tube can be bent in either direction with two degrees of freedom by mounting the bending device of the present invention to an examining insertion tube.

Also, control of the bending amount can be easily executed due to having a structure of bending by application of a tensile force to the wire. Furthermore, the mobile bending range can be set freely by varying the number of linked cylindrical members by having a structure that links multiple cylindrical members.

Also, conventionally, joints were rotatably linked or an applying means for bending motion was provided at each joint, but the present invention has a structure of linking the cylindrical members only with wires by utilizing wires which apply bending motion to the cylindrical members so the assembly can be implemented by inserting wires into the wire holding parts of the cylindrical members. Consequently, the manufacture of the linking structure can be reduced, the number of parts in the linking structure can be decreased, the productivity can be greatly improved, and reduction in the production cost can be achieved in comparison with conventional technology. Due to this high productivity, it is possible to favorably accommodate even for a disposable examining insertion tube due to sanitation reasons such as when conducting an examination through insertion into the inside part of a human body, etc.

Furthermore, in the present invention, a structure which mounts first and second small cylindrical members on the outer circumferential face of each cylindrical member and holds the wires in accordance with these is used. Each small cylindrical member can be later appended by soldering, adhesion, welding, etc., and [each] is attached on the outer circumferential face instead of inside the cylindrical member such that the manufacture thereof becomes very easy and achieving productivity improvement is possible. Also, fabricating a smaller cylindrical member than in the conventional technology becomes possible due to the ease in the manufacture thereof and contributes to the miniaturization of the device as a whole.

Also, in the case of a structure which inserts the wire in the first and second small cylindrical members, the wall thickness of the cylindrical member can be set to be thinner than when a through-hole for inserting the wire is provided in the cylindrical member itself.

By thus arranging the small cylindrical members on the outer circumferential face of the cylindrical member, a groove-shape space can be attained between the mutually adjacent small cylindrical members when multiple cylindrical members are linked. If the bending mechanism of the present invention is applied to an examining insertion tube, miniaturization in the major diameter of the examining insertion tube can be achieved by the amount that the wall thickness of the cylindrical member was made thin by arranging the constituent parts of the examining insertion tube in the aforementioned space. At the same time, making the weight of each cylindrical member light becomes possible.

Furthermore, when achieving miniaturization in the major diameter of the examining insertion tube, the constituent parts of the examining insertion tube are arranged naturally on the outside of the cylindrical member. An arrangement on the outside of the cylindrical member normally has flexibility so it is possible to provide softness to the feel from the outside part of the examining insertion tube when compared to the case of arranging the constituent parts of the examining insertion tube on the inside of the cylindrical member (due to the fact that though the aforementioned arrangement has a fixed softness due to its flexibility, the outer circumferential face of the cylindrical member does not normally have such flexibility).

Therefore, in the aforementioned arrangement, the feel on inserting the extreme end part side of the examining insertion tube has softness that is favorable when, for example, the examining object is a human body or an organism, and it becomes possible to easily execute the inserting operation itself Furthermore, each small cylindrical member is mounted on the outer circumferential face of the cylindrical member in the present invention so a greater distance can be attained from the first diameter or the second diameter of each cylindrical member to the wire compared to the case where each small cylindrical member is mounted on the inner circumferential face. Consequently, the bending moment for the cylindrical member becomes large when a tensile force is applied to each wire. In other words, applying the bending motion with less tensile force becomes possible. Therefore, executing the bending motion smoothly becomes possible and improvement in operability can be achieved.

In the invention, a flat face that is perpendicular to the center axis is provided at the extreme end of each projected part of the cylinder member so there is merit in the multiple linked cylindrical members being able to easily maintain an upright state since the flat faces of mutually adjacent cylindrical members make contact with the entire face by applying an equivalent tensile force to each wire.

In the invention, the wire holding part is composed of a small cylindrical member and the protruded section thereof is composed of the protruded part so all the parts can be formed easily, the two end faces are composed of smooth cylindrical shape members, the process of removing or cutting off becomes unnecessary, and higher productivity can be realized.

The present invention is constituted and functions as noted above such that a superior bending device for examining insertion tube not found conventionally can be provided.

What is claimed is:

1. A bending device for an examining insertion tube which is inserted in an examined object to inspect inside, said bending device operating to bend a head portion of the examining insertion tube, comprising:
   a plurality of cylindrical members; and
   four wires linking said cylindrical members in a cylindrical manner;
   wherein each of said cylindrical members comprises:
      two first protruding portions formed at both ends of a first diameter of said cylindrical member and protruding from a top end of said cylindrical member i an axial direction of said cylindrical member;
      two second protruding portions formed at both ends of a second diameter of said cylindrical member and protruding from a bottom end of said cylindrical member in the axial direction of said cylindrical member;
      two first small cylindrical members for two of the four wires to pass through, respectively, said two first small cylindrical members being fixed on an outer circumferential face of said cylindrical member and in vicinities of said first protruding portions, respectively; and
      two second small cylindrical members for the rest two of the four wires to pass through, respectively, said two second small cylindrical members being fixed on the outer circumferential face of said cylindrical member and in vicinities of said second protruding portions, respectively;
   wherein said first diameter is approximately perpendicular to the second diameter; and
   wherein said plurality of cylindrical members are linked by the wires, said first protruding portions of one cylindrical member contacting respectively said second protruding portions of another cylindrical member adjacent and above said cylindrical member.

2. The bending device for the examining insertion tube of claim 1,
   wherein said each protruding portion includes a flat face which is approximately perpendicular to the axial direction.

3. The bending device for the examining insertion tube of claim 1, further comprising four small tubes having approximately the same diameter as that of the small cylindrical member and extending from four small cylindrical members of the lowest cylindrical member such that each of the four wires consecutively pass through each small cylindrical member of said plurality of cylindrical members and each corresponding small tube of the said four small tubes.

4. The bending device for the examining insertion tube of claim 1, further comprising an operating mechanism around a bottom portion of the examining insertion tube to operate the bending device.

5. The bending device for the examining insertion tube of claim 3, further comprising an operating mechanism at a bottom of each of said small tubes to operate the bending device.

6. The bending device for the examining insertion tube of claim 1, further comprising:
   a flexible tube to cover an entire face of the examining insertion tube excluding head and bottom end faces; and
   a functional tube disposed on the outer circumferential face of said cylindrical member and inside said flexible tube, said functional tube elongating along said flexible tube.

7. A bending device for an examining insertion tube which is inserted in an examined object to inspect inside, said bending device operating to bend a head portion of the examining insertion tube, comprising:
   a plurality of cylindrical members; and
   four wires linking said cylindrical members in a cylindrical manner;
   wherein each of said cylindrical members comprises:
      two first small cylindrical members for two of said four wires to pass through, respectively, each of said two first small cylindrical members being fixed on an outer circumferential face at both ends of a first diameter of the cylindrical member, respectively, with an axial direction thereof aligned parallel to an axial direction of the cylindrical member and protruding from a top end of the cylindrical member;
      two second small cylindrical members for the rest two of said four wires to pass through, respectively, each of said two second small cylindrical members being fixed on an outer circumferential face at both ends of a second diameter of the cylindrical member, respectively, with an axial direction thereof aligned parallel to an axial direction of the cylindrical member and protruding from a bottom end of the cylindrical member;

wherein said first diameter is approximately perpendicular to said second diameter; and wherein said plurality of cylindrical members are linked by the wires, said first small cylindrical members contacting respectively said second small cylindrical members of another cylindrical member adjacent and above said one cylindrical member.

8. The bending device for the examining insertion tube of claim 7, wherein said each small cylindrical member includes a flat face on each protruding end which is approximately perpendicular to the axial direction of the cylindrical member.

9. The bending device for the examining insertion tube of claim 7, further comprising four small tubes having approximately the same diameter as that of the small cylindrical member and extending from four small cylindrical members of the lowest cylindrical member such that each of the four wires consecutively pass through each small cylindrical member of said plurality of cylindrical members and each corresponding small tube of the said four small tubes.

10. The bending device for the examining insertion tube of claim 7, further comprising an operating mechanism around a bottom portion of the examining insertion tube to operate the bending device.

11. The bending device for the examining insertion tube of claim 9, further comprising an operating mechanism at a bottom of each of said small tubes to operate the bending device.

12. The bending device for the examining insertion tube of claim 7, further comprising:

a flexible tube to cover an entire face of the examining insertion tube excluding head and bottom end faces; and a functional tube disposed on the outer circumferential face of said cylindrical member and inside said flexible tube, said functional tube elongating along said flexible tube.

* * * * *